United States Patent [19]

Haber et al.

[11] Patent Number: 4,890,627
[45] Date of Patent: Jan. 2, 1990

[54] MANUALLY EVACUATED SUCTION TUBE

[75] Inventors: Terry M. Haber, Lake Forest; Clark B. Foster, El Toro; William H. Smedley, Lake Elsinore, all of Calif.

[73] Assignee: Habley Medical Technology Corporation, Laguna Hills, Calif.

[21] Appl. No.: 118,759

[22] Filed: Nov. 9, 1987

[51] Int. Cl.⁴ .............................................. A61B 5/14
[52] U.S. Cl. ..................................... 128/765; 604/146
[58] Field of Search ..................... 128/760, 764, 765; 604/140–146, 121, 217, 220, 316

[56] References Cited

U.S. PATENT DOCUMENTS

| | | | |
|---|---|---|---|
| 2,688,325 | 9/1954 | Lockhart | 604/220 |
| 3,577,980 | 5/1971 | Cohen | 128/765 |
| 3,645,253 | 2/1972 | Goverde et al. | 128/765 |
| 3,937,211 | 2/1976 | Merten | 128/765 |
| 4,057,050 | 11/1977 | Sarstedt | 128/765 |
| 4,370,987 | 2/1983 | Bazell et al. | 128/765 |
| 4,766,908 | 8/1988 | Clement | 128/765 |

FOREIGN PATENT DOCUMENTS

WO82/04387  12/1982  World Int. Prop. O. .......... 128/765

Primary Examiner—Dalton L. Truluck
Attorney, Agent, or Firm—Morland C. Fischer

[57] ABSTRACT

A cylindrical, shatter-resistant, pre-sterilized suction tube in which a vacuum is to be selectively established by the user for automatically drawing a fluid sample, such as blood, or the like, by way of a hypodermic needle. The suction tube has a seal member detachably connected across a distal end thereof and a tab member detachably connected across a proximal end. A piston is located at the interior of the tube between the seal and tab members. An elongated retracting element extends between the detachable tab member and the piston. Application by the user of an axial pulling force to the tab member after the tab member has been detached from the proximal end of the suction tube causes a corresponding axial movement of the piston towards the open proximal end of the tube for expulsing air therefrom to evacuate the tube. The piston is locked at the proximal end to completely seal the tube and preserve the integrity of the vacuum which has been established therewithin.

18 Claims, 3 Drawing Sheets

MANUALLY EVACUATED SUCTION TUBE

BACKGROUND OF THE INVENTION

1. Field of the Invention

This invention relates to a unique, shatter-resistant suction tube, such as an evacuated blood collection tube, in which a vacuum is to be manually and selectively established by which the tube is automatically infused with a fluid (e.g. blood) sample by way of an associated hypodermic needle.

2. Prior Art

The practice of vacuum tube phlebotomy is a well-known art. That is to say, it is well-known to use a syringe having an evacuated blood collection tube by which blood can be drawn from a patient with a single veni-puncture, regardless of the number and type of blood samples required. The typical blood collection tube or vial has a self-sealing stopper located at an open end thereof to preserve a vacuum that has been mechanically established at the interior of the tube. One end of a double ended hypodermic needle penetrates the stopper and the other end penetrates the patient's vein to permit the tube to be automatically infused with a sample of the patient's blood. When a sufficient blood sample has been collected, the blood collection tube may be replaced with a new tube (so as to collect an additional sample) or the needle may be withdrawn from the patient's vein.

However, the conventional blood collection tube is evacuated by an array of frequently complex article handling and air evacuating equipment. The cost of manufacturing and maintaining such handling and vacuum producing equipment significantly contributes to the overall cost of the blood collection tube. Moreover, when a blood collection tube is stored for a long period of time prior to use, the rubber stopper may erode such that the vacuum/sterile environment of the tube may be jeopardized.

What is even more, the conventional blood collection tube is made of glass. Such tubes have been known to shatter when dropped or otherwise impacted by a shock transmitting force. Consequently, the possibility exists that the blood sample therewithin may leak or splatter which could contribute to the spread of a communicable and life threatening disease, such as AIDS, or the like.

SUMMARY OF THE INVENTION

In general terms, a pre-sterilized, shatter-resistant blood collection tube is disclosed in which a vacuum may be selectively established by the user for automatically drawing a blood sample from the vein of a patient. The tube is fabricated from a shatter-resistant (e.g. acrylic) material to substantially eliminate breakage and the spread of a communicable, and possibly life threatening, disease. The tube has a seal member connected across the distal end thereof and a tab member detachably connected across the proximal end. A piston is located at the interior of the tube between the distal seal and proximal tab members. A narrow, elongated retracting element extends through the interior of the tube between the detachable tab member and the piston. A locking pin is formed at one end of the retracting element and a receptacle is formed in the piston. The locking pin is removably received within the receptacle to permit the retracting element to be detachably connected to the piston.

In operation, the tab member is removed from the proximal end of the tube. An axial pulling force is applied, by a health care worker, to the tab member to correspondingly pull the piston axially and proximally through the tube, so that air ahead of the piston will be expulsed through the open proximal end. A proximal locking groove which extends peripherally around the interior of the tube receives and anchors the piston. With the piston anchored, an additional axial pulling force is applied to the tab member, whereby to remove the locking pin from its receptacle and thereby detach the retracting element from the piston. However, the tube is now evacuated with the distal and proximal ends thereof respectively closed and sealed by the seal member and piston. The evacuated suction tube is now adapted to be automatically infused with a sample of fluid (e.g. blood) via an associated hypodermic needle.

In accordance with another embodiment of the invention, where the evacuated suction tube is a blood collection tube, the seal member is detachable from the distal end of the tube and the piston member is detachable from the proximal end. The piston member has a hollow, open-ended chamber formed at a distal end thereof and an elongated pulling arm formed at a proximal end. A thixotropic gel, to which a catalysing agent is added, is located in the hollow chamber to induce the blood sample to coagulate and to form a barrier between the red blood cells and blood serum of the sample when the collection tube is centrifuged. The seal member may be grasped and removed from the distal end of the tube or the piston member may be grasped (at the pulling arm) and removed from the proximal end to permit the red blood cells and serum to be accessed independently and repeatedly from opposite ends of the tube.

DESCRIPTION OF THE PREFERRED EMBODIMENT

Figure 1:
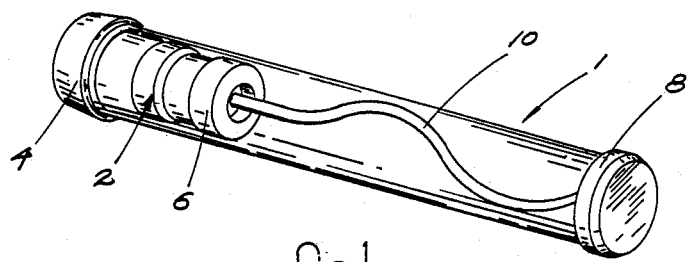
FIG. 1 is an isometric illustration of the manually evacuated suction tube which forms the present invention.

Referring now to the drawings, FIG. 1 shows a cylindrical, pre-sterilized suction tube 1 which forms the present invention. Suction tube 1 is preferably (and advantageously) formed from a clear, shatter-resistant polymer (e.g. acrylic). Located at the distal end of the suction tube 1 is an end plug 2. End plug 2 is preferably fabricated from a resilient, compressible material, such as rubber, or the like. As will be described in greater detail hereinafter, end plug 2 comprises a distal seal member 4 and a piston member 6. Seal member 4 is retained by an air-tight fit at the distal end of tube 1, so as to preserve a vacuum that is to be manually and selectively established within the tube in a manner that will be described when referring to FIGS. 4 and 5.

Located at the proximal end of suction tube 1 is a detachable sealing tab 8 which extends completely across the tube to preserve the sterilized condition thereof. By way of example, sealing tab 8 is fabricated from a woven plastic, fiber-like material that may be (e.g. heat) sealed across the proximal end of tube 1. A narrow, non-extensible retracting element 10 extends through the interior of suction tube 1 between the piston member 6 of end plug 2 and the proximal sealing tab 8. One end of retracting element 10 is integrally connected to the proximal sealing tab 8, while the opposite end of retracting element 10 is removably connected to piston member 6, in a manner that will soon be described.

Figure 2:
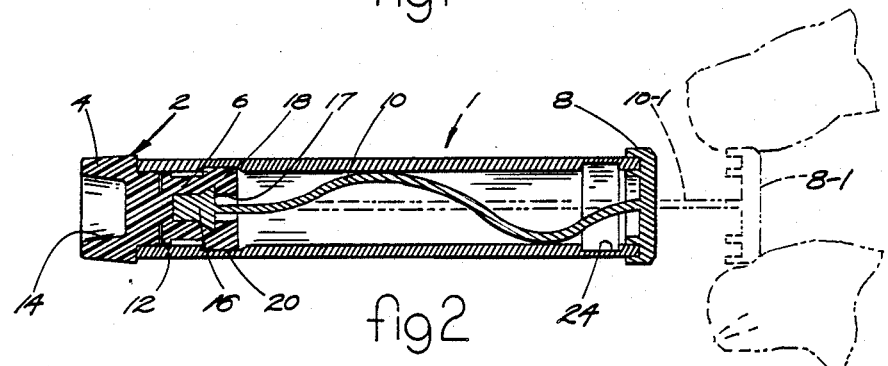
FIG. 2 is a cross-section of the suction tube of FIG. 1.
Figure 3:
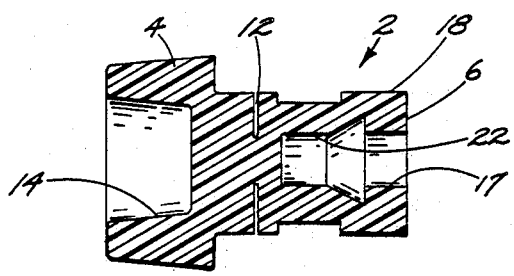
FIG. 3 is an enlarged cross-sectional view of a distal end plug of the suction tube of FIG. 1.

The details of the distal end plug 2 of suction tube 1 are now described while referring concurrently to FIGS. 2 and 3 of the drawings. As previously indicated, distal end plug 2 comprises a seal member 4 and a piston member 6. As is best illustrated in FIGS. 2 and 3, seal member 4 and piston member 6 are initially connected together to form a one-piece end plug 2. A tear plane 12 is formed through the approximate mid-point of distal end plug 2 in order that piston member 6 may be separated from and moved proximally relative to seal member 4. However, it is to be clearly understood that, instead of an integral distal end plug 2, as shown, the seal member 4 and piston member 6 may be initially separated from one another during the manufacture and assembly of suction tube 1.

The seal member 4 of end plug 6 includes a cylindrical needle docking cavity 14 which projects outwardly from the distal end of suction tube 1. Needle docking cavity 14 forms a target for receipt therethrough of one end of a double ended hypodermic needle (best illustrated in FIG. 6) to permit communication between the interior of tube 1 and a fluid to be collected (e.g. at the vein of a patient).

A conical locking pin 16 is integrally connected to one end of the retracting element 10. Piston member 6 includes a conical locking receptacle 22 which is sized for removable receipt of the locking pin 16 by way of a narrow channel 17 which communicates with locking receptacle 22 through piston member 6. Accordingly, retracting element 10 is detachably connected to piston member 6 when locking pin 16 is removably received in locking receptacle 22.

A coextensive lip 18 extends around the periphery of piston member 6. The peripheral lip 18 of piston member 6 is sized to be received within a peripheral positioning groove 20 (best shown in FIG. 2) which extends around the interior of the distal end of suction tube 1. End plug 2 is initially positioned within and retained at the distal end of tube 1 when the lip 18 of piston member 6 is received within the positioning groove 20.

A peripheral locking groove 24 (also best shown in FIG. 2) extends around the interior of the proximal end of suction tube 1 behind the proximal sealing tab 8. As will soon be described, piston member 6 of end plug 2 may be moved towards and anchored at the proximal end of tube 1, such that the lip 18 of piston member 6 is received within peripheral locking groove 24.

Figure 4:
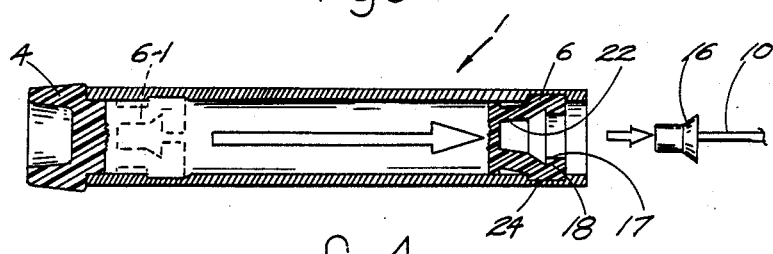
FIGS. 4 and 5 illustrate the operation of the suction tube.

The operation of the suction tube 1 by which a vacuum may be selectively established by the user is now described while referring concurrently to FIGS. 2, 3 and 4 of the drawings. Initially, the coextensive seal and piston members 4 and 6 of end plug 2 are retained at the distal end of tube 1. The piston member is illustrated in FIG. 4 in phantom at its initial distal position and designated by the reference numeral 6-1. The user grasps and removes the proximal sealing tab 8 and then applies an axial pulling force thereto, whereby to remove any slack from the retracting element 10 between sealing tab 8 and piston member 6-1. With the retracting element pulled taut (shown in phantom in FIG. 2 and designated 10-1), the user continues to apply an axial pulling force to the sealing tab (shown in phantom in FIG. 2 and designated 8-1) to generate a tearing force at the tear plane 12 of distal end plug 2. Accordingly, the coextensive seal and piston members 4 and 6 are separated from one another along tear plane 12.

The user continues to apply the axial pulling force to the sealing tab 8-1, until such force is sufficient to overcome the engagement between the peripheral lip 18 of piston member 6 and the distally located positioning groove 16 of suction tube 1. Accordingly, the now separated piston member 6-1 (of FIG. 4) is pulled proximally through the interior of tube 1. That is to say, with the locking pin 16 retained within locking receptacle 22, a proximal pulling force exerted by the user upon sealing tab 8 will be transferred to piston member 6 via retracting element 10 and locking pin 16, whereby to relocate piston member 6 from the distal end of the proximal end of the tube.

Figure 5:
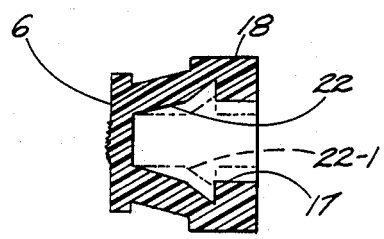

FIG. 5 shows the piston member 6 at rest and in a non-stressed configuration, such that the peripheral lip 18 thereof is received within the positioning groove 20 at the distal end of tube 1. However, when the peripheral lip 18 is removed from positioning groove 20 and piston member 6 is pulled proximally through tube 1, the resilient piston member assumes a stressed (i.e. compressed) configuration to make an air-tight fit with the interior walls of tube 1. That is to say, the compressive forces exerted upon piston member 6 by the interior walls of suction tube 1 when lip 18 is pulled out of positioning groove 20 cause the conical locking receptacle 22, at which conical locking pin 16 is removably received, to be rotated in a radially inward direction (shown in phantom and represented by reference numeral 22-1), whereby to prevent the removal of locking pin 16 from receptacle 22 as piston member 6 is pulled proximally through tube 1.

Air within suction tube 1 is expulsed (through the open proximal end thereof) ahead of the proximally sliding piston member 6. Accordingly, the suction tube 1 will be completely evacuated by the user when the piston member 6 is pulled to the proximal end of the tube.

After a sufficient axial pulling force has been applied to sealing tab 8 and retracting element 10, the piston member 6 will be relocated and anchored at the proximal end of suction tube 1 to preserve the integrity of the vacuum therewithin. More particularly, the spring-like memory of the resilient piston member 6 will cause the lip 18 thereof to rotate in a radially outward direction and into receipt by the peripheral locking groove 24 at the proximal end of suction tube 1, whereby to automatically return piston 6 to its initial non-stressed configuration, as shown in FIG. 5. The receipt of lip 18 in locking groove 24 anchors the piston member 6 at the proximal end of tube 1 and prevents any further axial displacement of the piston member 6 through the interior of tube 1.

However, the user continues to pull the sealing tab 8 and the retracting element 10 attached thereto in a proximal direction. With the piston member 6 anchored at the proximal end of suction tube 1, the proximal pulling force applied to sealing tab 8 will be transferred to locking pin 16 via retracting element 10. Accordingly, the locking pin 16 will now be removed from the locking receptacle 22 of piston member 6 via channel 17 (best represented in FIG. 4), when the proximal pulling force overcomes the engagement between pin 16 and receptacle 22. The integrally connected sealing tab 8, retracting element 10 and locking pin 16 may then be discarded. with sealing member 4 secured across the distal end of tube 1, piston member 6 anchored across the proximal end, and a vacuum established in the space therebetween, the suction tube 1 is now adapted to communicate with a hypodermic needle so that tube 1 may be automatically infused with a fluid sample.

Figure 6:
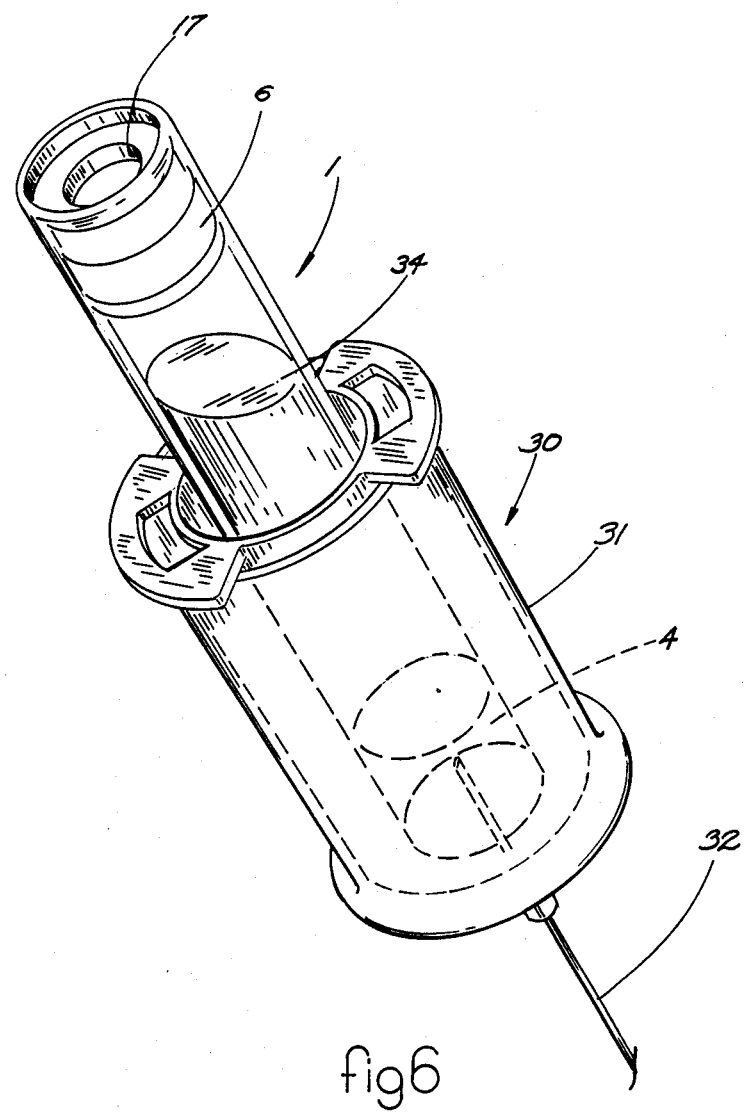
FIG. 6 shows the suction tube associated with a syringe assembly for drawing a blood sample by way of a hypodermic needle.

By way of example, one particular application for the suction tube 1 is the evacuated blood collection tube illustrated in FIG. 6 of the drawings. More particularly, and as will be known to phlebotomists, a syringe assembly 30 is provided included an outer sleeve 31 having open and closed ends. Evacuated blood collection tube 1 is positioned through the open end of the outer sleeve 31. A double ended hypodermic needle 32 is supported at the closed end of the outer sleeve 31, such that one end of the needle 32 extends proximally through the needle docking cavity (designated 14 in FIG. 2) of the distal sealing member 4, while the opposite end of needle 32 extends distally from the sleeve 31 to make a veni puncture. Thus, a sample of the patient's blood can be automatically drawn into the collection tube 1 via needle 32 for subsequent testing.

Figure 7:
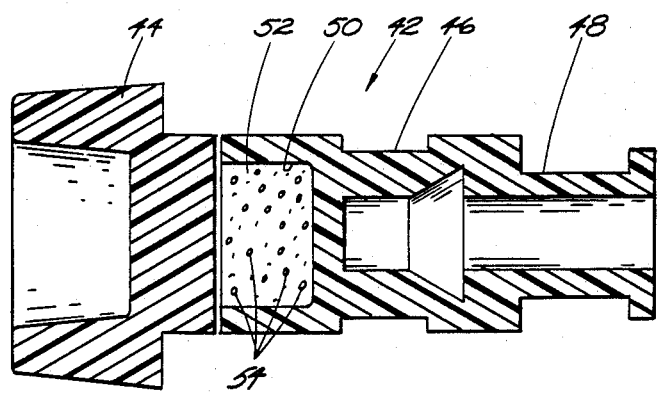
FIG. 7 is an enlarged cross-sectional view of a distal end plug of a suction tube which forms an alternate embodiment of the present invention.
Figure 8:
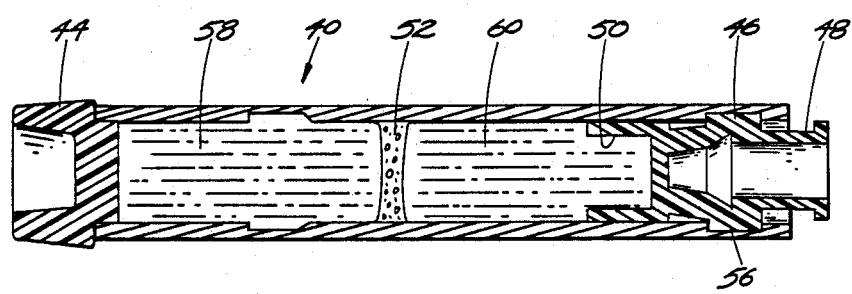
FIG. 8 is a cross-section of the suction tube which forms the alternate embodiment.

FIGS. 7 and 8 of the drawings illustrate an alternate embodiment of the manually evacuated suction tube 1 of FIGS. 1-6. In the event that the suction tube is to be used as a blood collection tube, the suction tube 40 of FIG. 8 will allow a blood sample to be centrifuged, whereby to separate the red blood cells and blood serum from one another. As was earlier disclosed, the suction tube 1 is preferably fabricated from a shatter-resistant material, such as acrylic. However, an acrylic material may not induce an adequate coagulation of the blood within the tube. The suction tube 40 of FIGS. 7 and 8 overcomes the foregoing problem and permits the patient's red blood cells and serum to be separated and accessed from opposite ends of the tube.

More particularly, the suction tube 40 is constructed in a substantially similar manner to the construction of tube 1. That is, an end plug 42 (of FIG. 7) is retained by an air-tight fit within the distal end of tube 40. However, unlike the end plug 2 of tube 1, end plug 42 includes a seal member 44 and a piston member 46 which are initially separated from one another. Moreover, a cylindrical gripping arm 48 is coextensively formed with and extended axially from the proximal end of piston member 46. The distal end of piston member 46 includes a hollow, open ended chamber 50 in which a thixotropic gel 52 is located. As will be known to those skilled in the art, the thixotropic gel 52 is a highly viscous polymer which has a density intermediate the densities of blood serum and red blood cells. In order to enhance the clotting of the blood sample within the acrylic tube 40, a catalysing agent 54 is added to gel 50. By way of example, catalysing agent 54 may be silicon, diatomaceous earth, thrombin, or the like.

In operation, the piston member 46 is pulled axially and proximally through the suction tube 40 (in a manner identical to that described when referring to the piston member 6 of tube 1) in order to manually evacuate tube 40. With sealing member 44 remaining secured across the distal end of tube 40, piston member 46 relocated and anchored (within locking groove 56) at the proximal end, the evacuated blood collection tube 40 is now adapted to communicate with one end of a double ended hypodermic needle (via distal seal member 44) of a syringe assembly (similar to that illustrated in FIG. 6), so that a sample of the patient's blood can be automatically drawn (at the opposite end of the needle) into tube 40 for subsequent testing.

The suction tube 40, in which a blood sample has been collected, may be removed from the syringe assembly and placed into a conventional centrifuge. The centrifugal force to which the tube 40 is subjected will cause an ejection of the thixotropic gel 52 from the hollow chamber 50 at the distal end of piston member 46 to establish a barrier between the patient's blood serum 58 and red blood cells 60. As an important advantage of the blood collection tube 40 of FIGS. 7 and 8 (and unlike conventional blood collection tubes in which one end thereof is always sealed), either end of tube 40 may be removed to permit the serum 58 or red blood cells 60 to be accessed independently and repeatedly. That is, seal member 44 may be grasped and removed from the distal end of tube 40 to permit access to the red blood cells 58, or the gripping arm 48 may be grasped, rotated, and pulled axially and proximally to free piston member 46 from the locking groove 56 at the proximal end of tube 40 and thereby permit access to serum 60.

By virtue of the present invention, the user (e.g. a health care worker) may manually and selectively evacuate the suction tubes 1 and 40 at a time when such section tubes are to be used. Therefore, expensive and complex handling and evacuating equipment, which have heretofore been utilized to evacuate conventional suction tubes, may be avoided. Moreover, the suction tubes 1 and 40 are fabricated from a shatter-resistant material, so as to reduce the possibility of spreading a contagious disease in the event that the tube is dropped while carrying a disease contaminated blood sample. What is more, since the tubes 1 and 40 need be evacuated only at the time of use, there is less opportunity for the seals to leak as a consequence of age, as is otherwise possible with conventional suction tubes that are mechanically evacuated and then stored for relatively long periods of time prior to use.

It will be apparent that while a preferred embodiment of the invention has been shown and described, various modifications additions may be made without departing from the true scope and spirit of the invention. For example, while the suction tube of the present invention has been described as having particular application as an evacuated blood collection tube, it is to be understood that said tube has other applications including, but not limited to, treating a snake bite, draining a cyst, draining a wound, taking a biopsy, or for esophogeal aspiration.

Having thus set forth a preferred embodiment of the invention, what is claimed is:

1. A suction tube in which a vacuum is to be established, said suction tube comprising:
a tube body having distal and proximal ends;

sealing means connected to said tube body to close the distal end thereof and to seal said distal end from the atmosphere;

end cap means detachably connected to said tube body to close the proximal end thereof and to seal said proximal end from the atmosphere;

piston means located at the interior of said tube body between said sealing means and said end cap means; and linking means extending through said tube body between said piston means and said detachable end cap means, such that the detachment of said end cap means from said tube body and the application of an axial pulling force to said end cap means causes a corresponding axial movement of said piston means towards the proximal end of said tube body, said piston means resealing the proximal end of said tube body from the atmosphere after the detachment therefrom of said end cap means.

2. The suction tube recited in claim 1, wherein said sealing means is detachable from the distal end of said tube body.

3. The suction tube recited in claim 1, further comprising means for removably connecting said linking means to said piston means.

4. The suction tube recited in claim 3, wherein said means for removably connecting includes a locking terminal extending from said linking means and a receptacle formed in said piston means, said terminal being releasably received within said receptacle.

5. The suction tube recited in claim 4, further comprising means to anchor said piston means at the proximal end of said tube body, such that the continued application of said axial pulling force to said end cap means after said piston means has been anchored causes the locking terminal of said linking means to be removed from the receptacle of said piston means.

6. The suction tube recited in claim 5, wherein said means to anchor includes a peripheral locking groove formed around the interior of said tube body and catch means extending from said piston means for receipt within said locking groove.

7. The suction tube recited in claim 1, wherein said piston means and said sealing means are detachably connected together at the distal end of said tube body with a tear plane formed therebetween, said piston means being separated from said sealing means along said tear plane when said piston means moves through said body.

8. The suction tube recited in claim 1, wherein said sealing means includes a needle locating cavity for receiving one end of a double ended hypodermic needle therethrough to permit communication with the evacuated interior of said tube body.

9. A syringe assembly for collecting a fluid sample and including an outer sleeve having opposing open and closed ends, a double ended hypodermic needle retained by the closed end of said outer sleeve, and an inner suction tube in which a vacuum is to be established, said inner tube extending through the open end of said outer sleeve and communicating with one end of said hypodermic needle so that said tube may be infused with a fluid sample, said inner suction tube comprising:

a tube body having distal and proximal ends in which to collect the fluid sample;

sealing means extending across said tube body to close the distal end thereof and to seal said distal end from the atmosphere;

closure means detachably connected to said tube body to close the proximal end thereof and to seal said proximal end from the atmosphere;

piston means located at the interior of said tube body between said sealing means and said closure means; and means interconnecting said detachable closure means with said piston means, such that a detachment of said closure means from said tube body and the application of an axial pulling force to said closure means causes a corresponding axial movement of said piston means towards the proximal end of said tube body for simultaneously establishing a vacuum in said tube body and resealing the proximal end of said tube body from the atmosphere.

10. The syringe assembly recited in claim 9, further comprising means to anchor said piston means at the proximal end of said tube body after said closure means has been removed from said proximal end and said piston means has been relocated thereto in response to said axial pulling force.

11. The syringe recited in claim 10, wherein said means interconnecting said closure means with said piston means is detachably connected to said piston means such that the continued application of said axial pulling force to said closure means after said piston means has been anchored causes said interconnecting means to become detached from said piston means.

12. The syringe assembly recited in claim 9, wherein said sealing means is removable from the distal end of said tube body and said piston means is removable from the proximal end of said tube body to permit access to the fluid sample collected within said tube body through either end thereof.

13. A blood collection tube for receiving a sample of blood to be centrifuged and separated into red blood cells and blood serum, said tube having distal and proximal ends and comprising:

sealing means detachably connected across the distal end of said tube;

piston means located at said distal end and movable through said tube to the proximal end thereof to expulse air from and thereby evacuate the interior of said tube; and means communicating with said tube for drawing a blood sample therewithin;

said sealing means being removable from the distal end of said tube and said piston means being removable from the proximal end of said tube after said blood sample has been centrifuged to permit independent access to the red blood cells or the serum, respectively, from opposite ends of the tube.

14. The blood collection tube recited in claim 12, wherein said piston means includes a hollow, open ended chamber in which to receive a thixotropic gel so as to form a barrier between the red blood cells and serum when the blood sample is centrifuged.

15. The blood collection tube recited in claim 14, further comprising a catalysing agent to be added to said thixotropic gel to induce the blood sample within said tube to clot, said catalysing agent including silica.

16. The blood collection tube recited in claim 14, further comprising a catalysing agent to be added to said thixotropic gel to induce the blood sample within said tube to clot, said catalysing agent including thrombin.

17. The blood collection tube recited in claim 13, wherein said piston means includes an axially extending pulling arm which may be grasped and pulled to remove said piston means from the proximal end of said tube.

18. The blood collection tube recited in claim 13, wherein said tube is manufactured from acrylic.

* * * * *